(12) United States Patent
Leproust

(10) Patent No.: US 8,415,138 B2
(45) Date of Patent: Apr. 9, 2013

(54) APPARATUSES AND METHODS FOR OLIGONUCLEOTIDE PREPARATION

(75) Inventor: Eric M. Leproust, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1758 days.

(21) Appl. No.: 11/469,405

(22) Filed: Aug. 31, 2006

(65) Prior Publication Data

US 2008/0058512 A1 Mar. 6, 2008

(51) Int. Cl.
*C12M 1/00* (2006.01)
*C12Q 1/68* (2006.01)
*C07H 19/00* (2006.01)
*C07H 21/00* (2006.01)
*B01J 10/00* (2006.01)
*B01J 19/00* (2006.01)
*B01J 19/18* (2006.01)

(52) U.S. Cl. ...... 435/283.1; 422/129; 422/131; 422/134; 435/287.2; 435/6.1; 536/22.1; 536/25.3

(58) Field of Classification Search .......... 435/6.1, 435/283.1, 287.2; 422/129, 131, 134; 536/22.1, 536/25.3
See application file for complete search history.

(56) References Cited

U.S. PATENT DOCUMENTS

| 4,373,071 A | 2/1983 | Itakura |
| 4,458,066 A | 7/1984 | Caruthers et al. |
| 4,500,707 A | 2/1985 | Caruthers et al. |
| 4,713,722 A | 12/1987 | Toyoda et al. |
| 4,973,679 A | 11/1990 | Caruthers et al. |
| 5,447,692 A * | 9/1995 | Keenan et al. ........... 422/116 |
| 5,681,534 A | 10/1997 | Neves |
| 5,807,525 A * | 9/1998 | Allen et al. ........... 422/131 |
| 6,033,631 A | 3/2000 | Zuckermann et al. |
| 6,100,522 A * | 8/2000 | Chiang ........... 250/288 |
| 6,384,210 B1 | 5/2002 | Blanchard |
| 6,419,883 B1 | 7/2002 | Blanchard |
| 6,461,571 B1 | 10/2002 | Tuffet et al. |
| 6,538,128 B1 | 3/2003 | Zhang et al. |
| 2002/0137074 A1* | 9/2002 | Piunno et al. ........... 435/6 |
| 2008/0262795 A1* | 10/2008 | Webb et al. ........... 702/184 |

FOREIGN PATENT DOCUMENTS

WO WO 95/25116 9/1995

OTHER PUBLICATIONS

Webster et al, Use of near infrared spectrometry for quantitative determinations of selamectin and moisture in topical formulations, 2003, Journal of Pharmaceutical and Biomedical Analysis, 33, 21-32.*
Dichloroethane, Sigma Aldrich brochure, Jan. 26, 2010.*
Aquastar c-400 titrator brochure, Jan. 26, 2010.*
ABI 394 DNA/RNA synthesizer brochure, printed Jan. 27, 2010.*

(Continued)

*Primary Examiner* — Dave Nguyen
*Assistant Examiner* — Narayan Bhat

(57) ABSTRACT

Provided are improved processes and apparatuses for solid phase oligonucleotide synthesis, the improvements comprising carrying out detritylation of the nascent oligonucleotide using a composition of an organic solvent, a protic solvent and a selected concentration, or selected concentration range, of water. In some embodiments, an oligonucleotide synthesis apparatus includes means for adding water to a detritylation reagent. In some embodiments, an apparatus can include a water detector for analyzing the water concentration of a detritylation reagent to be reacted with a nascent oligonucleotide. An apparatus can comprise a feedback loop to control the concentration of water at the point of the detritylation reaction and/or to control the detritylation reaction time. The apparatuses and methods reduce batch-to-batch variations in the manufacture of oligonucleotides immobilized on the surface of various substrates.

26 Claims, 3 Drawing Sheets

OTHER PUBLICATIONS

Nexus Glovebox brochure, printed Jan. 27, 2010.*
Manifold definition from the online Webster's at lionreference. chadwyck.com [retrieved on Aug. 10, 2010]. <URL:http://www. lionreference.chadwyck.com/search full text for manifold>. p. 1.*
Title: "ABI 3900 High-Throughput DNA Synthesizer", Specifications ucleic Acid Synthesis Products, Applied Biosystems.
Title: "Applied Biosystems 3400 DNA Synthesizer", Product Bullentin DNA Synthesis Instruments, Applied Biosystems.
Pon, Title: "Tips for Oligonucleotide Synthesis", pp. 1-8.
Title: "Detritylation DCA in DCM", Honeywell, MSDS No. DNA 0622, Current Issue Date: Sep. 2000, pp. 1-8.
Reddy et al., Title: "Moisture and Trace Metal Impurities in DNA Reagents and Their effect on DNA Synthesis", Feb. 28, 2005, Honeywell.
Title: "DNA Synthesis", e-oliogos DNA Synthesis, Sep. 1, 2006, pp. 1-6.
Title: "DNA Synthesis Reagents".
Title: "Material Safty Data Sheet", Matheson TRI Gas, pp. 1-8.
Title: "GEN Updates in Biotechnology: Oligonucleotides", pp. 1-8.
Forster et al., Title: "Dectection of Trace Levels of Water in Oil by Photoacoustic Spectroscopy", Sensors and Actuators B 77 (2001), pp. 620-624.
Title: "Trade Name: TCA Deblock Solution for DNA Synthesis", pp. 1-7.
Cary 50 UV-Vis Spectrophotometers, Varian, pp. 1-8.
Marche et al., Title: "Apparatus for Determination of Waster Solubiliy in Hydrocarborn: Toluene and Alklcylohexanes (C6 to C8) From 30 C to 180 C", J. Chem. Eng. Data, (2006), 51, pp. 355-359.
Title: "PID Controller", From Wikipedia, The Free Encyclopedia, Sep. 1, 2006, pp. 1-10.

* cited by examiner

APPARATUSES AND METHODS FOR OLIGONUCLEOTIDE PREPARATION

FIELD

The disclosure relates to the chemical synthesis of oligonucleotides and to methods, compositions, and apparatuses that are useful in such synthesis.

BACKGROUND

Oligonucleotides have become indispensable tools in modern molecular biology, being used in a wide variety of techniques, ranging from diagnostic probing methods to PCR to antisense inhibition of gene expression. This widespread use of oligonucleotides has led to an increasing demand for rapid, inexpensive and efficient methods for synthesizing oligonucleotides. The synthesis of oligonucleotides for antisense and diagnostic applications can now be routinely accomplished (see, e.g., Methods in Molecular Biology. Vol 20: Protocols for Oligonucleotides and Analogs pp. 165-189 (S. Agrawal, Ed., Humana Press, 1993); Oligonucleotides and Analogues: A Practical Approach pp. 87-108 (F. Eckstein, Ed., 1991); Agrawal and Iyer (1995) Curr. Op. in Biotech. 6:12; Antisense Research and Applications (Crooke and Lebleu, Eds., CRC Press, Boca Raton, 1993); Caruthers (1985) Science 230:281-285; Itakura et al., Ann. Rev. Biochem. 53: 323-356; Hunkapillar et al. (1984) Nature 310:105-110; and in "Synthesis of Oligonucleotide Derivatives in Design and Targeted Reaction of Oligonucleotide Derivatives (CRC Press, Boca Raton, Fla.) pages 100 et seq.; U.S. Pat. Nos. 4,458,066; 4,500,707; 5,153,319; 5,869,643; EP 0294196). Early synthetic approaches included phosphodiester and phosphotriester chemistries. Khorana et al., J. Molec. Biol. 72: 209 (1972) discloses phosphodiester chemistry for oligonucleotide synthesis. Reese (1978) Tetrahedron Lett. 34:3143-3179, discloses phosphotriester chemistry for synthesis of oligonucleotides and polynucleotides. These early approaches have largely given way to the more efficient phosphoramidite and H-phosphonate approaches to synthesis. Beaucage and Caruthers (1981) Tetrahedron Lett. 22:1859-1862, discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Machines for the automated synthesis of support-bound single stranded DNA have been described (see, e.g., Matteucci and Caruthers (1981) J. Amer. Chem. Soc. 103:3185-3191; and Gait, ed., Oligonucleotide Synthesis: A Practical Approach (IRL Press, Washington, D.C., 1984)). A synthetic cycle is repeated under computer control to add one nucleoside monomer unit at a time to achieve the desired sequence and length which defines the oligonucleotide. For example, within the phosphoramidite, or phosphite triester, synthetic cycle several reactions can be used:

I. Deprotect the reactive functionality (usually a 5' hydroxyl) on the growing chain;
II. Achieve coupling by the addition of a monomer and activator;
III. Cap unreacted 5' hydroxyls to prevent further coupling to failure sequences;
IV. Oxidize the newly formed internucleotide phosphorous linkage to the naturally occurring pentacoordinate state; and
V. Optionally cap unreacted 5' hydroxyls to prevent further coupling to failure sequences and to remove water introduced by the oxidation reaction.

In some applications, an oligonucleotide is synthesized on a solid support such as in an array. Oligonucleotide arrays (such as DNA or RNA arrays), are known and are used, for example, as diagnostic or screening tools. Such arrays include regions of usually different sequence oligonucleotides arranged in a predetermined configuration on a substrate. These regions (sometimes referenced as "features") are positioned at respective locations ("addresses") on the substrate. The arrays, when exposed to a sample, will exhibit an observed binding pattern. This binding pattern can be detected upon interrogating the array. For example all polynucleotide targets (for example, DNA) in the sample can be labeled with a suitable label (such as a fluorescent compound), and the fluorescence pattern on the array accurately observed following exposure to the sample. Assuming that the different sequence oligonucleotides were correctly deposited in accordance with the predetermined configuration, then the observed binding pattern will be indicative of the presence and/or concentration of one or more polynucleotide components of the sample.

Oligonucleotide arrays can be fabricated using in situ synthesis methods (see, e.g., WO 95/25116 and WO 98/41531, and the references cited therein). The in situ method for fabricating an oligonucleotide array typically follows, at each of the multiple different addresses at which features are to be formed, the same conventional sequence used in forming oligonucleotides on a support by means of known chemical processes as described above.

SUMMARY

In some embodiments, the present disclosure provides improved methods for solid phase oligonucleotide synthesis. In these improved methods, the improvement comprises carrying out detritylation of the nascent oligonucleotide using a composition of an organic solvent, a protic solvent and water. In some embodiments, the composition comprises an organic solvent, a protic acid, and water present at a concentration within a selected range, or above a selected cut-off value. For example, the water concentration can be in the range of about 100 ppm (100 µg/ml) to about 3000 ppm. In some embodiments, the range is about 200 ppm to about 500 ppm. In some embodiments, the water concentration is above 100 ppm. Exemplary protic acids include monochloroacetic acid, dichloroacetic acid and trichloroacetic acid. In some embodiments, the concentration of the protic acid is in the range from about 0.05% mole fraction to about 25.0% mole fraction.

In some embodiments, there are provided methods for minimizing batch-to-batch variation of manufactured oligonucleotides, the method comprising requesting a selected range of water concentration in a lot of detrilyation reagent from a supplier. In some embodiments, a selected minimal concentration is requested. In some embodiments, a selected maximal concentration of water in a detritylation reagent is requested, and an end-user adds water to within a selected range.

In some embodiments, there are provided improved apparatuses for performing oligonucleotide synthesis. In some embodiments, an improved apparatus comprises a continuous on-line water detector for analyzing water in a detritylation reagent, wherein the water detector is located upstream from the point of the detritylation reaction. In some embodiments, an improved apparatus comprises a water detector, a compatible water containing reagent and, upstream from the water detector, means for mixing a detritylation reagent with the water containing reagent. In some embodiments, a control unit receives signals representative of the detected water concentration from the water detector and uses these signals in a feedback loop to correct the water concentration in the detritylation reagent prior to the point of the detritylation reaction.

In some embodiments, there are provided apparatuses and methods for modulating the reaction time of a detritylation reaction based on the water concentration of detritylation reagent used in the reaction.

The processes, apparatuses, and compositions for as disclosed herein provide improved consistency in the batch-to-batch manufacture of oligonucleotides.

DETAILED DESCRIPTION

Figure 1:
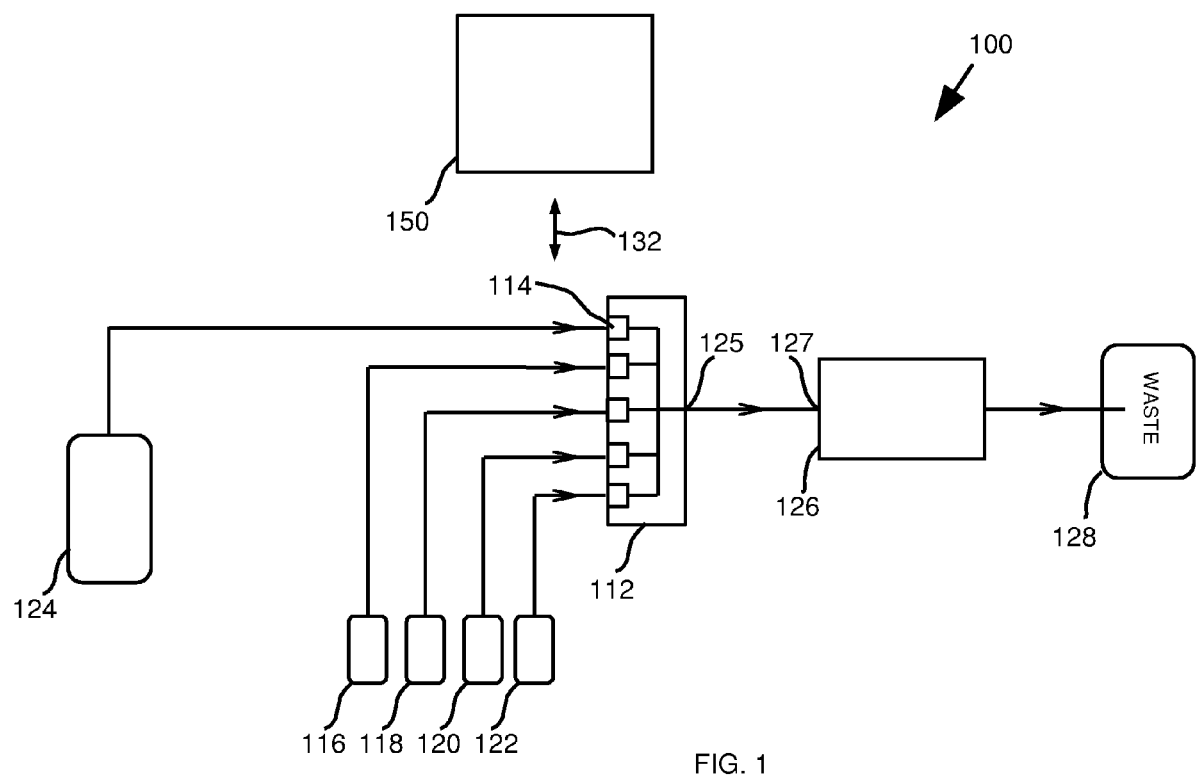
FIG. 1 shows a fluidic schematic view of some embodiments of an oligonucleotide synthesizer.

Before describing the present disclosure in detail, it is to be understood that this disclosure is not limited to specific compositions, method steps, or equipment, as such can vary. It is also to be understood that the terminology used herein is for the purpose of describing particular embodiments only, and is not intended to be limiting. Methods recited herein can be carried out in any order of the recited events that is logically possible, as well as the recited order of events. Furthermore, where a range of values is provided, it is understood that every intervening value, between the upper and lower limit of that range and any other stated or intervening value in that stated range is encompassed within the present disclosure. Also, it is contemplated that any optional feature of the inventive variations described can be set forth and claimed independently, or in combination with any one or more of the features described herein.

Unless defined otherwise below, all technical and scientific terms used herein have the same meaning as commonly understood by one of ordinary skill in the art to which this disclosure belongs. Still, certain elements are defined herein for the sake of clarity.

All literature and similar materials cited in this application, including but not limited to patents, patent applications, articles, books, treatises, and internet web pages, regardless of the format of such literature and similar materials, are expressly incorporated by reference in their entirety for any purpose. In the event that one or more of the incorporated literature and similar materials differs from or contradicts this application, including but not limited to defined terms, term usage, described techniques, or the like, this application controls.

The publications discussed herein are provided solely for their disclosure prior to the filing date of the present application. Nothing herein is to be construed as an admission that the present disclosure is not entitled to antedate such publication by virtue of prior invention. Further, the dates of publication provided can be different from the actual publication dates, which can need to be independently confirmed.

It must be noted that, as used in this specification and the appended claims, the singular forms "a", "an" and "the" include plural referents unless the context clearly dictates otherwise. Thus, for example, reference to "a biopolymer" can include more than one biopolymer.

Definitions

The following definitions are provided for specific terms that are used in the following written description.

A "biopolymer" is a polymer of one or more types of repeating units. Biopolymers are typically found in biological systems and particularly include polynucleotides as well as their analogs such as those compounds composed of or containing amino acid analogs or non-amino acid groups, or nucleotide analogs or non-nucleotide groups. As such, this term includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions, or in non-Watson-Crick type hydrogen bonding and/or electrostatic interactions (for example, but not limited to, Hoogsten binding and the like). Polynucleotides include single or multiple stranded configurations, where one or more of the strands can or can not be completely aligned with another. Specifically, a "biopolymer" includes deoxyribonucleic acid or DNA (including cDNA), ribonucleic acid or RNA and oligonucleotides, regardless of the source.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

A "biomonomer" references a single unit, which can be linked with the same or other biomonomers to form a biopolymer (for example, a single nucleotide with two linking groups one or both of which can have removable protecting groups).

A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally or non naturally occurring polynucleotides in a sequence specific manner analogous to that of two naturally occurring polynucleotides. Nucleotide sub-units of deoxyribonucleic acids are deoxyribonucleotides, and nucleotide sub-units of ribonucleic acids are ribonucleotides.

An "oligonucleotide" generally refers to a nucleotide multimer of about 10 to 200 nucleotides in length, while a "polynucleotide" or "nucleic acid" includes a nucleotide multimer having any number of nucleotides.

A chemical "array", unless a contrary intention appears, includes any one, two or three-dimensional arrangement of addressable regions bearing a particular chemical moiety or moieties (for example, biopolymers such as polynucleotide sequences) associated with that region, where the chemical moiety or moieties are immobilized on the surface in that region. By "immobilized" is meant that the moiety or moieties are stably associated with the substrate surface in the region, such that they do not separate from the region under conditions of using the array, e.g., hybridization and washing and stripping conditions. As is known in the art, the moiety or moieties can be covalently or non-covalently bound to the surface in the region. For example, each region can extend into a third dimension in the case where the substrate is porous while not having any substantial third dimension measurement (thickness) in the case where the substrate is non-porous. An array can contain more than ten, more than one hundred, more than one thousand more than ten thousand features, or even more than one hundred thousand features, in an area of less than 20 $cm^2$ or even less than 10 $cm^2$. For example, features can have widths (that is, diameter, for a round spot) in the range of from about 10 µm to about 1.0 cm. In other embodiments each feature can have a width in the range of about 1.0 µm to about 1.0 mm, such as from about 5.0 µm to about 500 µm, and including from about 10 µm to about 200 µm. Non-round features can have area ranges equivalent to that of circular features with the foregoing width (diameter) ranges. A given feature is made up of chemical moieties, e.g., nucleic acids, that bind to (e.g., hybridize to) the same target (e.g., target nucleic acid), such that a given feature corresponds to a particular target. At least some, or all, of the features are of different compositions (for example, when any repeats of each feature composition are excluded the remaining features can account for at least 5%, 10%, or 20% of the total number of features). Interfeature areas will typically (but not essentially) be present which do not carry any polynucleotide. Such interfeature areas typically will be present where the arrays are formed by processes involving drop deposition of reagents but may not be present when, for example, light directed synthesis fabrication processes are used. It will be appreciated though, that the interfeature areas, when present, could be of various sizes and configurations. An array is "addressable" in that it has multiple regions (sometimes referenced as "features" or "spots" of the array) of different moieties (for example, different polynucleotide sequences) such that a region at a particular predetermined location (an "address") on the array will detect a particular target or class of targets (although a feature can incidentally detect non-targets of that feature). The target for which each feature is specific is, in representative embodiments, known. An array feature is generally homogenous in composition and concentration and the features can be separated by intervening spaces (although arrays without such separation can be fabricated).

The phrase "oligonucleotide bound to a surface of a solid support" or "probe bound to a solid support" or a "target bound to a solid support" refers to an oligonucleotide or mimetic thereof, e.g., PNA, LNA or UNA molecule that is immobilized on a surface of a solid substrate, where the substrate can have a variety of configurations, e.g., a sheet, bead, particle, slide, wafer, web, fiber, tube, capillary, microfluidic channel or reservoir, or other structure. In some embodiments, the collections of oligonucleotide elements employed herein are present on a surface of the same planar support, e.g., in the form of an array. It should be understood that the terms "probe" and "target" are relative terms and that a molecule considered as a probe in certain assays can function as a target in other assays.

"Addressable sets of probes" and analogous terms refer to the multiple known regions of different moieties of known characteristics (e.g., base sequence composition) supported by or intended to be supported by an array surface, such that each location is associated with a moiety of a known characteristic and such that properties of a target moiety can be determined based on the location on the array surface to which the target moiety binds under stringent conditions.

In some aspects, the present disclosure concerns methods and apparatuses useful for oligonucleotide synthesis.

In some embodiments, there are provided herein improved processes and apparatuses for solid phase oligonucleotide synthesis. In these improved processes and apparatuses, the improvement comprises carrying out detritylation of the nascent oligonucleotide having at least one trityl group using a composition comprising a protic acid, a protic solvent, and an organic solvent. In some embodiments of these processes, such synthesis is carried out using the phosphoramidite, H-phosphonate, or phosphotriester approach. In some embodiments, such synthesis may be solid phase synthesis or solution phase synthesis. A "nascent oligonucleotide having one or more trityl group" is intended to include any oligonucleotide in which at least one trityl moiety protects at least one hydroxy functionality. A trityl group can comprise trityl, monomethoxytrityl, dimethoxytrityl, 9-phenylxanthen-9-yl or 9-p-methoxyphenylxanthen-9-yl, for example.

Applicant has observed that the use of certain lots of detritylation reagent obtained commercially caused reduction in the yield of full length of oligonucleotides chemically synthesized on a substrate, apparently due to depurination. While using a given detritylation reagent lot, the process performance appeared stable, however, when the detritylation lot used was switched to a different one, the overall performance, while still stable, was significantly different from that of the previous lot. The present disclosure is based in part on the surprising discovery by Applicant that variations in the concentration of water in the different lots of detritylation reagent correlated with the observed lot-to-lot variation in performance.

Without wishing to be bound by theory, it is contemplated that the reaction to be performed (detritylation) and the reaction to be avoided (depurination) are acid catalyzed, and the effective acidity of the solution is modulated by the amount of water present. As water is added to the detritylation solution, it solvates the acid and reduces the availability of the acidic proton to participate in other reactions. It is contemplated, and has been experimentally verified, that addition of water reduces the efficiency of the detritylation reaction, as would be expected from the solvation effect. By similarity, it can be inferred that the depurination side reaction can also be modulated by variable amount of water in the detritylation solution. Overall, the present disclosure solves the problem of variable oligonucleotide synthesis performance due to variations in detritylation lot composition, more precisely due to variations in the water content variation. In addition, the detritylation reaction is a very subtle process to optimize and control since the reagent degrades the product of the reaction. In other words, after completion of the detritylation reaction, the product formed is a detritylated growing chain, ready for the coupling of the base n+1. However, even after completion of the detritylation reaction, this product is still subject to the depurination side reaction, which can depurinate and ultimately cleave any A bases synthesized prior to base n. Therefore, it is important to control the reaction conditions so that the detritylation can be completed without any substantial depurination happening. As described above, both reactions are acid catalyzed. However, for a given condition, the depurination side reaction is less favored than the detritylation side reaction. (Primarily detritylation and only fractions of depurination have been observed). Hence, the depurination side reaction requires a higher effective acidity and, if the effective acidity of the detritylation solution is reduced, the efficiency of the depurination side reaction would be relatively more depressed that the efficiency of the detritylation solution (due to the non linearity of the acid based reaction as a function of pH). The presently disclosed methods and apparatuses allow the manufacturing process to diminish the above described lot-to-lot performance variations, or, in other words, allow a more stable manufacturing process. The instant methods and apparatuses allow a decrease in the extent of depurination and the synthesis of oligonucleotides of higher sequence integrity (i.e. lower fractions of failure sequences).

In some embodiments, a composition used in a detritylation reaction as described herein includes water. The amount of water that can be utilized during a detritylation step can be determined by routine experimentation, such as by titration. For example, detritylation reagent can be prepared with various concentrations of water, and the effect on the detritylation reaction can be monitored over time. Suitable duration and temperature for a detritylation step can also be determined by routine experimentation.

In some embodiments, detritylation of a nascent oligonucleotide having one or more trityl group can be carried out in a composition comprising an organic solvent, a protic acid, and water. In some embodiments, the water is present at a concentration greater than 100 ppm. In some embodiments, the water is present at a concentration greater than 300 ppm. In some embodiments, the water is present at a concentration in the range of 100 ppm to 3000 ppm, at a concentration in the range of 100 ppm to 2000 ppm, at a concentration in the range of 200 ppm to 500 ppm, at a concentration in the range of 100 ppm to 200 ppm, or at a concentration in the range of 140 ppm to 160 ppm.

In some embodiments of the improved processes according to the present disclosure, the detritylation step utilizes a protic acid as a detritylation reagent. As used herein, a protic acid is intended to mean a compound in which hydrogen is attached to oxygen or nitrogen and which has appreciable acidity. In some embodiments, the protic acid is present in the range from 0.625% mole fraction to 25.0% mole fraction, in the range from 1.25% mole fraction to 12.5% mole fraction, in the range from 0.01% mole fraction to 25.0% mole fraction, or in the range from 0.1% mole fraction to 12.5% mole fraction. In some embodiments, the protic acid is present in the range from 0.01% mole fraction to 25.0% mole fraction. In some embodiments, the protic acid is present in the range from 0.1% mole fraction to 12.5% mole fraction. In some embodiments, the protic acid is present at a concentration of about 3.75% mole fraction. Non-limiting examples of a protic acid include a halogenoacetic acid, such as, for example, a chloroacetic acid, a bromoacetic acid, or a fluoroacetic acid. For example, a protic acid can comprise at least one of monochloroacetic acid, dichloroacetic acid (DCA) and trichloroacetic acid (TCA). A protic acid can comprise at least one of trifluoroacetic acid, formic acid, sulfuric acid, propanoic acid, para-toluenesulfonic acid and benzenesulfonic acid. In some embodiments, hydrochloric acid can be used.

A wide variety of organic solvents can be used in a composition used in a detritylation reaction as described herein. There are no particular limits on the organic solvent that can be used, as long as it does not interfere with the chemical synthesis of the polynucleotide and as long as the intended reaction can be performed efficiently. In some embodiments, an organic solvent is a liquid hydrocarbon. The organic solvent can comprise, for example, an alkane, a halo-substituted hydrocarbon solvent, a chlorohydrocarbon solvent, or an arene solvent. An organic solvent can comprise at least one of toluene, dichloromethane, dichloroethane, aliphatic substituted benzene, halogenic solvent, 1,2-dichloroethane, and methylene chloride.

In some embodiments, the organic solvent is an alkylbenzene. The aklylbenzene can have a single phenyl ring. Examples of suitable alkylbenzenes include, without limitation, toluene, xylene, hemimellitene, pseudodocumene, mesitylene, prehnitene, isodurene, durene pentamethylbenzene, hexamethylbenzene, ethylbenzene, ethyltoluene, propylbenzene, propyltoluene, butylbenzene, pentanylbenzene, pentanyl toluene, hexanyl benzene and hexanyl toluene. In some embodiments, alkylbenzenes include those having more than one phenyl ring, such as diphenylmethane, triphenylmethane, tetraphenylmethane and 1,2-diphenylethane can be used, examples of which include, without limitation, styrene, stilbene, diphenylethylene, triphenylethylene and tetraphenylethylene. In some embodiments, alkynylbenzenes can be used, and include, without limitation, phenylacetylene and diphenylacetylene.

There are no particular limits on the support used in the chemical synthesis of polynucleotides used in the apparatuses and methods described herein, as long as the support is compatible with the reaction solvents and other reagents utilized in the synthesis. The substrates may be fabricated from a variety of materials. A wide variety of organic polymers or inorganic polymers can be employed (see, e.g., U.S. Pat. Nos. 4,373,071; 4,500,707; 6,171,797; and 6,538,128).

One embodiment of the present disclosure concerns methods for ensuring that the water concentration of a detritylation reagent is consistent from lot-to-lot and is within a pre-selected range. In obtaining a detritylation reagent lot from a supplier, a specified concentration can be requested by the user. In some embodiments, a user can request that a detritylation reagent be supplied having a concentration of water that is below a predetermined cut-off value. A user can request that the supplier spike water into the reagent to achieve a desired water concentration, or range of concentration. In some embodiments, a user can spike-in water to achieve a desired water concentration.

In some embodiments, a detritylation reagent can be requested from a supplier, and the water content can be specified as indicated hereinabove. The detritylation reagent can be tested for water (by a supplier and/or user) concentration using one or more of a variety of methods and analyzers. Non-limiting examples of such methods and devices include Karl Fischer titration (see. e.g., U.S. Pat. Nos. 5,340,541; 6,946,298; 7,049,146; and product descriptions by Brinkmann, Mettler-Toledo, Sigma-Aldrich, and Metrohm), photoacoustic spectroscopy (Foster et al. (2001) Sensors and Activators B 77:620-628), electrode impedance, and calorimetric tests (see, e.g., U.S. Pat. Nos. 3,799,846; 4,696,931; 5,229,295; and 5,454,258). In some embodiments, the detection can use a moisture detecting cell such as described in U.S. Pat. No. 3,799,846. In some embodiments, a method and analyzer such as described in U.S. Pat. No. 5,107,118 can be used to detect and measure water content of a sample based on infrared absorption.

In some embodiments, the subject apparatus is an apparatus for synthesizing oligonuclotides where the apparatus includes a manifold, a source of detritylating reagent upstream of the manifold and a conduit for operatively connecting the manifold to the source of detritylating reagent, and means for measuring the water concentration of detritylating reagent in the conduit.

In certain embodiments, the subject apparatus includes a source of a compatible aqueous reagent capable of mixing with the detritylating reagent to form a mixture where the water concentration in the mixture is higher than the detritylating reagent, where the apparatus includes means for mixing the compatible aqueous reagent with detritylating reagent in the conduit to form a mixture.

Referring to FIG. 1, there are shown some embodiments of a conventional oligonucleotide synthesizer 100, comprising a valve manifold 112 comprising a plurality of controlled valves, such as shown at valve 114, each valve of which is connected by conduit to a respective reagent container. Manifold 112 is in fluid communication, via outlet port 125, with reactor chamber 126 having reactor inlet 127, reactor outlet 129, and waste reservoir 128. In some embodiments, reactor chamber 126 is configured to hold a pre-packaged reactor column (not shown). Such reactor columns can comprise standard, commercially available reactor columns for oligonucleotide synthesis manufactured by a variety of chemical providers such as, for example, Prime Synthesis, Applied Biosystems, Inc., and Perseptive BioSystems, Inc. Such prepackaged reactor columns can be provided with a substrate having a first 3' base covalently attached thereto. In some embodiments, chamber 126 comprises a flow-cell configured to retain a planar support, such as a glass or polymeric support, for array manufacture, such as by ink-jet methods, as described hereinabove. Each valve, such as valve 114, is in fluid communication via conduit for receiving fluid containing a stream of reagent from a reagent container or tank. Non-limiting examples of such reagents include detritylation (deblocking) reagent 124, acetonitrile 116, oxidizer 118, capping reagent 120, and ancillary reagent 122. Other liquid reagents can comprise various phosphoramidites (not shown). The liquid reagents can be held under positive pressure by a dry inert gas, such as nitrogen or argon. The oligonucleotide synthesis apparatus 100 can also include a router for internet connection (not shown), a personal computer (PC) 150. The PC can control the high level operation of the synthesizer through interface 132. This operation can comprise the submitting of synthesis jobs and the monitoring of the sequence progression, as well as detecting any fault conditions. The PC can control the operation of the valve manifold and coordinates the manifold with the synthesis jobs being sent through the synthesizer.

In some embodiments, the reactor chamber 126 is configured to accommodate a pre-packaged reactor column (not shown). In normal operation, the synthesizer can be programmed to cause a stream of reagents to flow through the inlet 127, said stream containing the necessary reagents for the elongation of the oligonucleotide molecule covalently attached to a support contained in the reactor column. The stream of reagents is delivered to the column inlet in a series of cycles, each cycle including, for example, the reaction steps I.-V. indicated hereinabove. The oligonucleotide is elongated by one base by every cycle. The assemblage of cycles, the quantity of the stream of reagents and the effective residence time presented to the reactor column are commonly referred to as the protocol.

Figure 2:
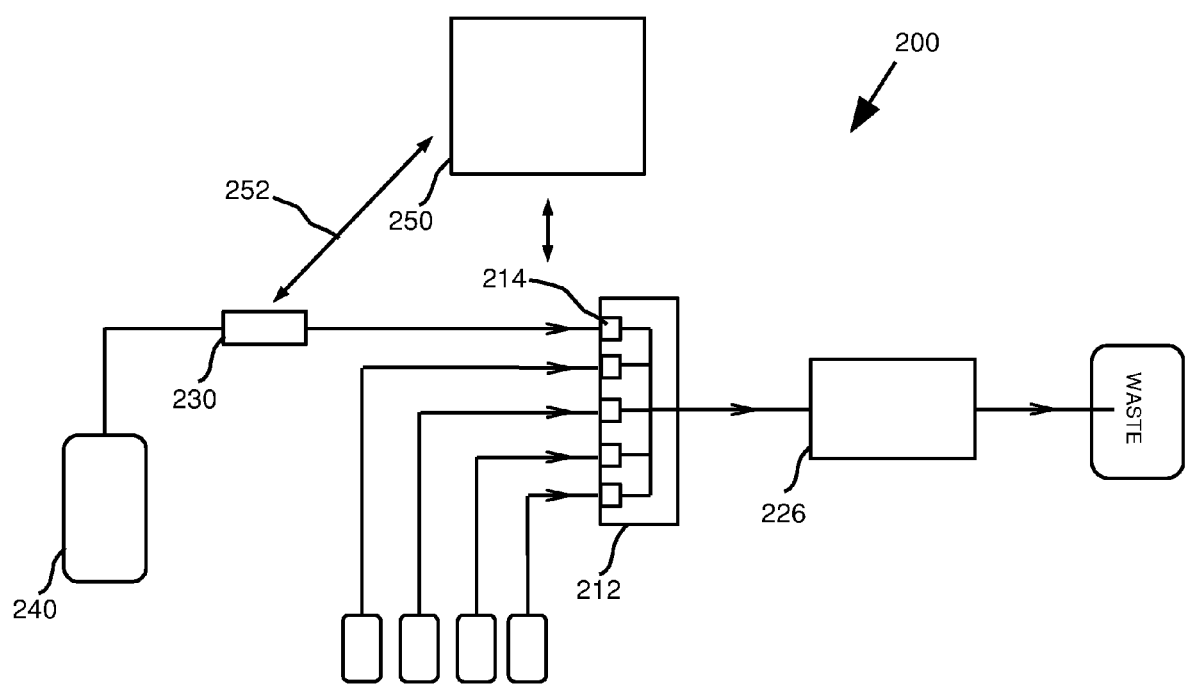
FIG. 2 shows a fluidic schematic view of some embodiments of an oligonucleotide synthesizer including a water detector.

Referring to FIG. 2, there are shown some embodiments of an oligonucleotide synthesizer 200, comprising a valve manifold, and reactor chamber (as also shown in FIG. 1). In some embodiments, apparatus 200 comprises a water detector 230 downstream of detritylation reagent 240. A non-limiting example of such a detector comprises an infrared absorption spectrophotometer. In some embodiments, the water detector 230 can comprise an in-line detector. The measurement can be discontinuous, intermittent or continuous. Non-limiting examples of suitable in-line detectors include a Varian 3100 FTIR (Excalabur Series) and a Cary 50 UV-Vis (Varian). A detector having fiber optic probes can be used to make the measurement away from the detector itself. The water detector can be linked via interface 252 with computer 250 for calculating the actual water content of the sample in response to the electrical signal received from water detector 230. The water detector can be calibrated with solutions containing known amounts of water and the resulting calibration constant stored for use in converting the measured signals for unknown samples to their corresponding water concentration.

In some embodiments, an algorithm can be used for activating an alarm and/or interrupting a synthetic protocol if the water content of the detritylation reagent falls out of a predetermined range. In some embodiments, standard algorithms, such as feedback loops, can be used to adjust the detritylation reaction time at the point-of-reaction (POR) (i.e., in reactor chamber 226) in real-time by control of valve manifold 214 under control of computer 250. For example, a standard proportional-integral (PI) control algorithm can be used for manipulating the detritylation reaction time, although any other suitable control algorithm can be used.

Figure 3:
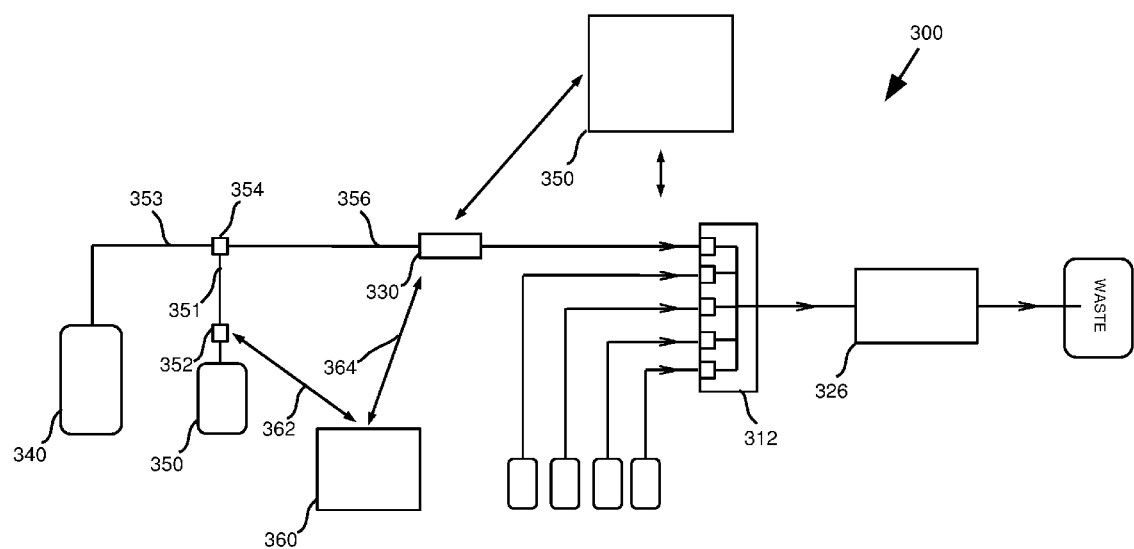
FIG. 3 shows a fluidic schematic view of some embodiments of an oligonucleotide synthesizer including a water containing reagent and a water detector.

Referring to FIG. 3, there are shown some embodiments of an oligonucleotide synthesis apparatus 300, comprising a valve manifold 312, and reactor chamber 326. In some embodiments, apparatus 300 comprises a water detector 330 downstream of detritylation reagent 340. A compatible aqueous reagent 350 is fluidly connected via conduit 351 to conduit 353. "Compatible aqueous reagent" refers to a reagent containing water and suitable for mixing with a detritylation reagent as described herein to increase the water concentration of the mixture. Non-limiting examples of a compatible aqueous reagent include purified water (e.g., deionized water), organic solvent plus water, or detriylation reagent plus water. Mixing device 354 mixes detrilyation reagent 340 with aqueous reagent 350. One embodiment of such a mixing device is a conventional mixing tee. Mixing tees and mixing crosses are available commercially (e.g. Upchurch Scientific). Non-limiting examples of suitable mixing devices include: a mixing tee as described in U.S. Pat. No. 6,100,522 and as available commercially (e.g. part no. P-632 Upchurch); a mixing cross (part no. P-634, Upchurch); a "Y" union; a multiport union having one outlet and greater that two inlets; a multiple inlet mixing valve (part no. 080T-3-12-32-5, BioChem Valve Corporation); a switching valve (part no. V-100T, Upchurch), and a static mixer (Koflo).

A closed feedback loop system can be used to maintain a constant concentration of water at the POR and to dampen out variations in the incoming supply chain. Control of valve 352 is effected by means of servo controller 360. Controller 360 can be a PID (proportional, integral, derivative), a P (proportional), or a PI (proportional, integral) type, although any suitable controller can also be used. The input of the controller 360 is connected via interface 364 to water analyzer 330, and its output is connected to via interface 362 with valve 352. By way of example, in operation, the output of analyzer 330 is converted to a standardized signal, and controller 360 compares the signal supplied by analyzer 330 with a desired signal, and supplies to valve 352 an analog signal which is proportional to the difference between the actual signal and the desired signal. The desired signal can correspond to the signal for a range, or to the signal for a cut-off value, of water concentration in the detritylation solution under analysis in conduit 356.

Controller 360 can be a stand-alone component, can interface with computer 350. In some embodiments, computer 350 can be configured to be used as the controller.

In some embodiments, valve 352 can be replaced by an injector configured for injecting aqueous reagent under control of controller 360. The valve or injector can only add water, and not subtract any, so the water specification of the incoming detritylation solution will preferably be lower than the selected water specification at the POR.

The processes and apparatuses as described herein are useful for synthesizing polynucleotides, including oligonucleotides, on a scale ranging from small laboratory scale to large commercial scale. The processes and apparatuses can be used to supply oligonucleotides for research purposes, for diagnostic purposes and for therapeutic purposes with improved consistency between batches of manufactured oligonucleotides.

Those skilled in the art will recognize that many equivalents to the products and processes according to the invention can be made by making insubstantial changes to such products and processes. The following claims are intended to encompass such equivalents.

What is claimed is:

1. An apparatus for synthesizing an oligonucleotide, the apparatus comprising:
   a manifold,
   a source of detritylating reagent upstream of said manifold,
   a conduit that operatively connects said manifold to said source of detritylating reagent,
   means for measuring the water concentration of detritylating reagent in said conduit between said manifold and said source of detritylating reagent,
   a source of a compatible aqueous reagent that is:
      a) operatively connected to said conduit by a controllable valve, and
      b) upstream of said means for measuring water concentration, and
   a valve controller that is operatively connected to said controllable valve and said means for measuring water concentration,
   wherein said valve controller maintains said water concentration of said detritylating reagent above a selected minimal concentration.

2. The apparatus of claim 1, wherein said detritylating reagent comprises a composition suitable for detritylating a nascent oligonucleotide having one or more trityl group.

3. The apparatus of claim 2, wherein the water concentration is in the range from 100 ppm to 3000 ppm.

4. The apparatus of claim 3, wherein the water concentration is in the range from 100 ppm to 500 ppm.

5. The apparatus of claim 1, wherein said detritylating reagent comprises:
   an organic solvent,
   a protic acid in the range from 0.0125% mole fraction to 12.5% mole fraction, and
   water at a concentration greater than 100 ppm.

6. The apparatus of claim 1, wherein said means for measuring water concentration comprises an inline detector.

7. The apparatus of claim 6, wherein said means for measuring water concentration comprises an infrared detector.

8. The apparatus of claim 7, wherein said detector comprises fiber optics.

9. The apparatus of claim 7, comprising a computer for controlling said manifold and for receiving data from said detector.

10. The apparatus of claim 7, wherein said means for measuring water concentration comprises a computer and wherein said computer is configured for calculating the water concentration in said detritylation reagent in response to electrical signals received from said detector.

11. The apparatus of claim 10, wherein said computer comprises a feedback loop algorithm for calculating a detritylation reaction time dependent upon the concentration of water in said detritylating reagent.

12. The apparatus of claim 11, wherein said algorithm comprises a PID (proportional, integral, derivative).

13. The apparatus of claim 6, wherein said apparatus further comprises a computer for controlling said manifold and for receiving data from said detector.

14. The apparatus of claim 13, wherein said computer is interfaced with said detector and with said valve controller, wherein said means for measuring water concentration comprises said computer and wherein said computer is configured for calculating the water concentration in said detritylation reagent in response to electrical signals received from said detector.

15. The apparatus of claim 14, wherein said computer comprises a feedback loop algorithm for regulating said valve dependent upon the concentration of water in said mixture in order to maintain a selected concentration of water in said mixture.

16. The apparatus of claim 15, wherein said algorithm comprises a PID (proportional, integral, derivative).

17. The apparatus of claim 15, wherein said water concentration is in the range of between 100 ppm and 500 ppm.

18. The apparatus of claim 1, wherein said source of a compatible aqueous reagent is capable of mixing with said detritylating reagent to form a mixture whereby the water concentration in the mixture is higher than said detritylating reagent.

19. The apparatus of claim 18, wherein said aqueous reagent comprises water.

20. The apparatus of claim 19, wherein said aqueous reagent comprises water mixed with an organic solvent.

21. The apparatus of claim 19, wherein said aqueous reagent comprises water mixed with a detritylating reagent.

22. The apparatus of claim 18, comprising means for mixing said compatible aqueous reagent with detritylating reagent in said conduit to form a mixture.

23. The apparatus of claim 22, comprising, upstream of said detector and in fluidic communication with said conduit, means for mixing said compatible aqueous reagent with said detritylating reagent in said conduit.

24. The apparatus of claim 23, wherein said means for mixing comprises a mixing tee.

25. The apparatus of claim 24, comprising a conduit connecting said source of aqueous reagent with said mixing tee.

26. The apparatus of claim 18, wherein said source of compatible aqueous reagent comprises a syringe.

* * * * *